United States Patent [19]

Mansat

[11] Patent Number: 4,728,329
[45] Date of Patent: Mar. 1, 1988

[54] PROSTHETIC BAND

[75] Inventor: Christian Mansat, Balma, France

[73] Assignees: Sulzer Brothers Ltd., Winterthur; Protek AG, Berne, both of Switzerland

[21] Appl. No.: 853,617

[22] Filed: Apr. 18, 1986

[30] Foreign Application Priority Data

May 3, 1985 [CH] Switzerland ............... 1891/85

[51] Int. Cl.$^4$ ............................................. A61F 2/08
[52] U.S. Cl. ............................................ 623/13; 623/11
[58] Field of Search ............ 623/13, 1, 12, 11; 128/334 R, DIG. 14, DIG. 21, 335.5

[56] References Cited

U.S. PATENT DOCUMENTS

| | | | |
|---|---|---|---|
| 4,246,660 | 1/1981 | Wevers | 623/13 |
| 4,301,551 | 11/1981 | Dore et al. | 623/13 |
| 4,483,023 | 11/1984 | Hoffman, Jr. et al. | 623/13 |
| 4,511,706 | 4/1985 | Shalaby et al. | 123/335.5 X |
| 4,584,722 | 4/1986 | Levy et al. | 623/13 |

Primary Examiner—Richard J. Apley
Assistant Examiner—Alan W. Cannon
Attorney, Agent, or Firm—Kenyon & Kenyon

[57] ABSTRACT

The prosthetic band is formed of concentric flexible sleeve-like elements formed of braided filaments for use as a transverse ligament for a knee joint. The band has a central flexible zone having a longitudinal stretchability of from 5 to 25 percent in response to a tension of 50 N/square millameters while also having relatively rigid end zones for anchoring to a bone. The flexible zone of the band can be drawn into a bore in a bone while under tension and, upon release of the tension, the flexible zone will swell up in the bore to ensure intimate contact with the bone tissue.

15 Claims, 3 Drawing Figures

PROSTHETIC BAND

This invention relates to a prosthetic band. More particularly, this invention relates to a prosthetic band which is capable of use as a prosthetic tendon.

Heretofore, it has been known to construct bands of synthetic materials, for example, in the form of sleeve-like textile structures for use as prosthetic bands. For example, French Pat. No. 7818385 (2,395,012) describes a prosthetic tendon consisting of braided plastic yarns and covered by a removable covering coated with pyrolytic carbon. In order to copy the characteristics of a natural tendon, the angle of braiding may be varied so that the flexibility and the longitu-dinal stretch of the prosthetic tendon can be varied in an end zone in which the prosthetic tendon is connected to an incomplete natural tendon requiring replacement. However, in the actual operative zone, i.e. outside the end zones which are required for connection to the natural tendon, the prosthetic tendon has a constant cross-section and, thus, constant flexibility and consistent longitudinal stretch with the longitudinal stretch being very limited.

U.S Pat. No. 3,176,316 describes a prosthetic tendon which is of fundamentally similar construction and which is constructed of synthetic fibers which are braided or woven to form a flexible sleeve. The operative zone of this tendon is a relative compact "shaft" without longitudinal stretch and of at least substantially constant diameter. At the ends, the tendon takes the form of a relatively loose hollow flexible sleeve which can be drawn over the stump of a natural tendon which requires replacement.

It has been found that the flexibility and longitudinal stretch of the known constructions are insufficient for artificial bands, for example, for transverse ligaments and lateral ligament of the knee joint.

Accordingly, it is an object of the invention to provide a prosthetic band having considerable longitudinal stretch, considerable flexibility and relatively high torsional rigidity in the operative zone.

It is another object of the invention to provide a prosthetic band which is capable of a high degree of stretchability and flexibility in an operative zone while having relatively rigid anchorage zones.

It is another object of the invention to provide a prosthetic band of relatively simple construction which is characterized in a high degree of flexibility and stretchability in an operative central zone.

Briefly, the invention provides a prosthetic band which is comprised of a plurality of concentric sleeve-like elements which define a shaft having a central flexible zone and a pair of rigid end zones. In addition, the flexible zone has a diameter of from 1:2 to 2.0 times the diameter of a respective end zone and is axially stretchable; the number of sleeve-like elements is constant throughout said zones.

In the case of sleeve-like textile structures which are built up without a core from a number of concentric layers, the relatively small increase in diameter provides a con-siderable increase in flexibility and longitudinal stretch. The minimum longitudinal stretch value provided by the band is, for example, in the flexible zone of from 5% to 25% in response to tensions of 50 N/square millimeters.

Advantageously, the shaft comprises braided sleeve-like elements having braiding angles to the axial direction which vary in the zones of different flexibilities but are the same for all the sleeve-like elements in any one zone. These sleeve-like elements can be produced from multifilament or monofilament yarns. The term "monofilament yarn" includes metal wires while the term "yarn" includes yarns of natural fibers, for example of silk, or synthetic fibers, for example polyester, polyethylene or known resorbable materials. In order to produce a central shaft or strand, a number of concentric sleeve-like elements or layers, for example from twenty to thirty such elements are "layered" one above another in the case of a transverse ligament for a knee joint.

Very satisfactory results in the production of braided sleeve-like elements have been achieved using twisted yarns comprising a large number, for example sixty, monofilaments made, for example, of polyester, and having diameters of from 0.01 to 0.03 millimeters. Advantageously, in order to increase the mechanical strength and/or to produce a very dense braiding to ensure a relatively dense and smooth surface, the outermost sleeve-like element can be made of yarns having a larger number of monofilaments, for example, twice as many monofilaments.

For replacement of a transverse or cruciate ligament of a knee joint, low-flexibility zones are disposed on either side of a high-flexibility zone. In this case, the diameter of the untensioned central shaft or strand in the high-flexibility zone is 8 millimeters. Advantageously, the longitudinal stretch of the flexible zone is such that, in response to a tensile loading of 500 N, the diameter of the two zones are at least substantially equal.

The prosthetic band requires a very simple implantation technique, for example, for the replacement of the anterior transverse ligament of a knee joint. By way of example, with the prosthetic band comprised of a flexible central part or shaft merging at both ends into a rigid end zone, the prosthetic band can be clamped fast externally at one end to the tibia and at the other end to the femur by means of a brace or agraffe hammered into the bone. Initially, one end of the band may be secured to the tibia by hammering in of an agraffe. Thereafter, the free end of the band is bent and recessed into a bore in the tibia bone. Next, the flexible zone is lead through a bore in the tibia, the diameter of the tibia bore being smaller than the diameter of the flexible zone when the flexible zone is not in tension. When tension is applied, and because of the longitudinal stretch, the diameter of the band decreases so that the band can be readily drawn through the bore. When the tension ceases, the band "swells" and makes intimate contact with the bone inside the bore thus promoting the ongrowth and ingrowth of tissue. After emerging from the bore in the tibia, the band extends between the condyles, extends some way around the lateral condyle in the dorsal zone and is clamped fast externally to the femur laterally thereof by an agraffe in the manner described.

These and other objects and advantages of the invention will become more apparent from the following detailed description taken in conjunction with the accompany drawings wherein.

Figure 3:
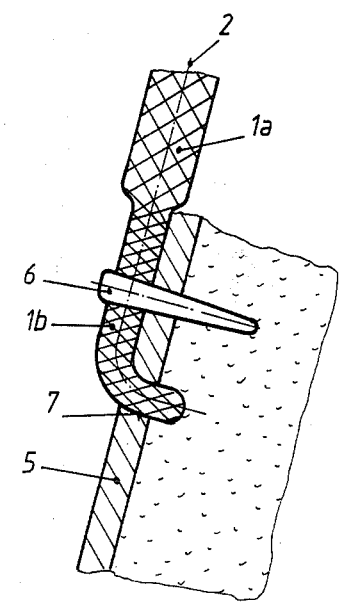

FIG. 3. illustrates a part cross sectional view of one end of the prosthetic band secured to a bone in accordance with the invention.

Figure 1:
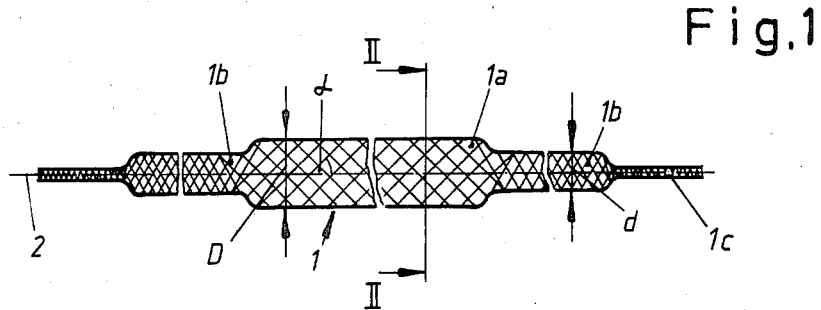
FIG. 1 illustrates a diagrammatic view to approximately normal size of a prosthetic band constructed in accordance with the invention.

Referring to FIG. 1, the prosthetic band 1 is constructed and sized, for example, for use as a cruciate ligament in a knee joint. As illustrated, the band 1 has a central flexible zone 1a of a diameter D which merges at each end into a rigid end zone 1b of a diameter d. To this end, each end zone 1b has a relatively reduced flexibility with respect to the central zone 1a.

The diameter D of the central flexible zone 1a is in the range of from 1.2 to 2.0 times the diameter d of the end zone 1b. For example, in the case of the illustrated band 1 which is substantially drawn to normal size and which is intended to replace a transverse or cruciate ligament, the diameter D of the flexible zone 1a is approximately 12 millimeters and the diameter d of each rigid zone 1b is approximately 7 millimeters corresponding to a ratio of approximately 1.7.

The band 1 also has thin leader parts 1c extending from each rigid zone 1b. Each of these leader parts 1c can, in certain circumstances can be reinforced by an inlay or by impregnation in a hardening composition.

The central flexible zone 1a also has an increased degree of longitudinal stretch relative to the rigid end zones 1b. The differences in the longitudinal stretch and flexibility of the zones 1a and 1b are achieved by differences in the braiding angle relative to the axis 2 of the band 1 when the band 1 is built up from braided sleeve-like elements 3. The flexibility is greater in proportion as the braiding angle $\alpha$ to the axis 2 is flatter.

Figure 2:
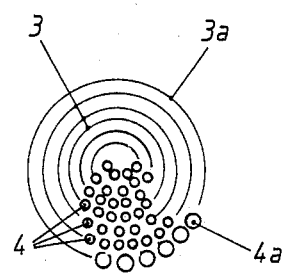
FIG. 2 illustrates a view taken on line II—II of FIG. 1.

As indicated in FIG. 2, the prosthetic band 1 is made up of a plurality of concentric sleeve-like elements. Further, the number of elements remains constant throughout the end zones 1b and the central zone 1a. Within the leader parts 1c, the number of sleeve-like elements may be reduced. Further, each element is braided at a constant braiding angle to the axial direction in each respective zone relative to the other elements in the respective zone. That is, within the central zone 1a all of the sleeve-like elements have the same braiding angle. However, the braiding angle in the central zone is less than in each rigid end zone of a respective sleeve-like element 3.

The number of concentric sleeve-like elements 3 which are provided are sufficient to provide a longitudinal stretch which should be at least from 5% to 25% in response to a loading of 50 N/square millimeters.

Each sleeve-like element 3 is made up of discrete yarns 4 which, for example, may be twisted from a number of monofilaments to form a multifilament yarn. In order to ensure that the band 1 has a relatively dense and smooth surface in the flexible zone 1a, the yarns 4a of the outermost sleeve 3a are thicker, i.e. these yarns are of greater cross-section than the yarns in the inner elements 3 by having twice as many monofilaments.

When the band is stretched, for example, under a tensile loading of 500 N, the diameter of the central zone 1a reduces substantially to the diameter of a rigid end zone 1b. Although the diameter of the central zone has been exemplified as approximately twelve millimeters, the diameter may range from 8 to 12 millimeters in the unstressed state.

Referring to FIG. 3, in order to secure the prosthetic band 1 to a bone 5, a brace or agraffe 6 is hammered through an end zone 1a into the bone 5 in order to secure the rigid zone 1b to the bone 5. At a few centimeters outside the agraffe 6, the rigid zone 1b is severed by a sharp cutting tool, such as a scalpel, and recessed into a previously provided bore 7 in the bone 5. With the opposite end secured in like manner, the band 1 can be firmly secured in place.

When implanted as a transverse ligament in a knee joint, the central zone 1a is able to flex and stretch under the action of the knee joint during use while the rigid zones 1b remain rigid and fixedly secured to the tibia and femur.

The invention thus provides a prosthetic band which has considerable longitudinal stretch and considerable flexibility within the central zone while having relatively rigid end zones provided for a secure anchorage of the band. In addition, the central zone has a relatively high degree of torsional rigidity due to the concentric nature of the braided sleeves from which the band is constructed.

Further, the invention provides a prosthetic band which can be readily constructed by concentric sleeve-like textile structures. In this respect, the term "sleeve-like textile structure" denotes "hollow cylinders" prepared from multifilament yarns or from monofilaments such as wires. Further, these yarns may be worked up by any known yarn-working procedures, such as braiding or weaving or knitting or the like so as to permit the band to have at least a minimum of longitudinal stretch, for example of from 5 to 25 percent in response to tensions of 50 N/square millimeters.

What is claimed is:

1. A prosthetic band comprising a plurality of concentric sleeve-like elements defining a shaft having a central flexible zone and a pair of rigid end zones, said central flexible zone having a diameter of from 1.2 to 2.0 times the diameter of a respective rigid end zone, said central zone being axially stretchable.

2. A prosthetic band as set forth in claim 1 wherein each element is braided at a constant braiding angle to an axial direction in each respective zone relative to the other elements in said respective zones, said braiding angle being less in said central flexible zone than in each rigid end zone of a respective element.

3. A prosthetic band as set forth in claim 1 wherein each element is formed of multifilament yarns.

4. A prosthetic band as set forth in claim 3 wherein each yarn is twisted.

5. A prosthetic band as set forth in claim 1 wherein each element is formed of yarns with the outermost element having yarns of greater cross-section than the remaining elements.

6. A prosthetic band as set forth in claim 1 wherein said flexible zone is followed by a rigid zone.

7. A prosthetic band as set forth in claim 1 wherein said flexible zone has a diameter of from 8 to 12 millimeters in an unstressed state.

8. A prosthetic band as set forth in claim 1 wherein said flexible zone is responsive to a tensile loading of 500 N to stretch to a reduced diameter substantially equal to the diameter of a rigid end zone.

9. A prosthetic band as set forth in claim 1 wherein the number of said elements is constant throughout said zones.

10. A prosthetic band comprising a plurality of equal length concentric sleeve-like elements defining a shaft having an axially stretchable and flexible central zone and a pair of rigid end zones, said central flexible zone having a diameter of from 1.2 to 2.0 times the diameter of a respective end zone.

11. A prosthetic band as set forth in claim 10 wherein each element is braided at a constant braiding angle to an axial direction in each respective zone relative to the other elements in said respective zones, said braiding angle being less in said central flexible zone than in each rigid end zone of a respective element.

12. A prosthetic band as set forth in claim 10 wherein said central zone is responsive to a tensile loading of 500 N to stretch to a reduced diameter substantially equal to the diameter of a rigid end zone.

13. A prosthetic band comprising a plurality of equal length concentric sleeve-like elements defining a shaft having an axially stretchable and flexible central zone and a pair of rigid end zones, said central flexible zone having a diameter of from 8 to 12 millimeters in an unstressed state and each end zone has a diameter of approximately 7 millimeters.

14. A prosthetic band as set forth in claim 13 wherein said element is braided at a constant braiding angle to an axial direction in each respective zone relative to the other elements in said respective zones, said braiding angle being less in said central flexible zone than in each rigid end zone of a respective element.

15. A prosthetic band as set forth in claim 13 wherein said central zone is responsive to a tensile loading of 500 N to stretch to a reduced diameter substantially equal to the diameter of a rigid end zone.

* * * * *

UNITED STATES PATENT AND TRADEMARK OFFICE
CERTIFICATE OF CORRECTION

PATENT NO. : 4,728,329

DATED : March 1, 1988

INVENTOR(S) : Christian Mansat

It is certified that error appears in the above-identified patent and that said Letters Patent is hereby corrected as shown below:

```
In the Abstract, line 6 "millameters" should be -millimeters-
Column 1, line 15 "longitu-dinal" sholud be -longitudina-
Column 1, line 37 "ligament" should be -ligaments-
Column 1, line 61 "con-siderable" should be -considerable-
```

Signed and Sealed this

Twenty-third Day of August, 1988

Attest:

DONALD J. QUIGG

Attesting Officer

Commissioner of Patents and Trademarks